United States Patent [19]

Petitpierre

[11]  4,183,553

[45]  Jan. 15, 1980

[54] PRESSURE- OR HEAT-SENSITIVE RECORDING MATERIAL AND NOVEL CHROMANO COMPOUNDS USED THEREIN

[75] Inventor: Jean C. Petitpierre, Kaiseraugst, Switzerland

[73] Assignee: Ciba-Geigy Corporation, Ardsley, N.Y.

[21] Appl. No.: 873,628

[22] Filed: Jan. 30, 1978

[30] Foreign Application Priority Data

Feb. 4, 1977 [CH] Switzerland .................. 1380/77

[51] Int. Cl.² ................ B41L 1/20; C07D 311/60
[52] U.S. Cl. ................................ 282/27.5; 106/21; 260/345.2; 427/151; 428/307; 428/913; 428/914; 542/454; 542/455; 542/401
[58] Field of Search .............. 542/454, 455, 401; 428/913, 307, 411, 914, 537; 260/345.2; 282/27.5; 106/21; 427/151

[56] References Cited

U.S. PATENT DOCUMENTS

| | | | |
|---|---|---|---|
| 3,407,145 | 10/1968 | Buile | 542/401 UX |
| 3,666,525 | 5/1972 | Kimura et al. | 260/345.2 X |
| 3,812,157 | 5/1974 | Lin et al. | 260/345.2 |
| 3,955,026 | 5/1976 | Matsukawa et al. | 428/913 X |
| 3,984,583 | 10/1976 | Hermans et al. | 428/913 X |
| 4,039,207 | 8/1977 | Ishizuka | 428/913 X |
| 4,052,218 | 10/1977 | Samat et al. | 542/401 X |

OTHER PUBLICATIONS

Malkin et al., "Thermochromic and Photochemical Properties of Bis(spiropyrans)", in Chem. Abs., 85:64775u, vol. 85, 1976.
Dorion et al., "Photochromism", The Focal Press, New York, 1970, pp. 11, 18-21.
Zwanenburg et al., "Photochromic Chromenes", in Chem. Abs. 85:123806e, vol. 85, p. 633, 1976.
Zwanenburg, et al., "Photochromic Chromenes", in Chem. Abs. 83:61622q., p. 176, 1975.
1972-1976 Chem. Substance Index Chem. Abs.

Primary Examiner—Arthur P. Demers
Attorney, Agent, or Firm—Prabodh I. Almaula

[57] ABSTRACT

A pressure- or heat-sensitive recording material which contains as color former at least one chromano compound of the general formula

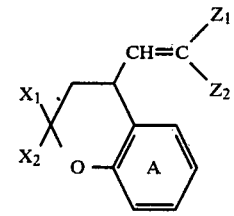

wherein
$X_1$, $X_2$, $Z_1$ and $Z_2$, each independently of the other, represent the group of the formula

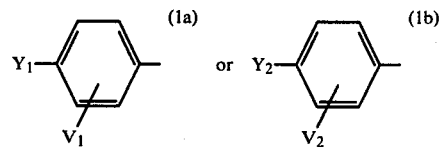

in which
$V_1$ and $V_2$, each independently of the other, represent hydrogen, halogen, lower alkyl or lower alkoxy, and
$Y_1$ and $Y_2$, each independently of the other, represent hydrogen, —O—$R_1$ or

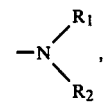

and the ring A is unsubstituted or substituted by halogen, nitro, lower alkyl, —O—$R_3$ or

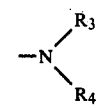

or contains a fused benzene ring, while
$R_1$, $R_2$, $R_3$ and $R_4$, each independently of the other, represent hydrogen, alkyl of not more than 12 carbon atoms which is unsubstituted or substituted by halogen, hydroxyl, cyano or lower alkoxy, or represent cycloalkyl, phenyl, benzyl, or phenyl or benzyl which is substituted by halogen, nitro, lower alkyl or lower alkoxy, or
each of the pair of substituents
$R_1$ and $R_2$ and $R_3$ and $R_4$, together with the nitrogen atom to which said pair is attached, independently represents a 5- or 6-membered heterocyclic radical.

25 Claims, No Drawings

PRESSURE- OR HEAT-SENSITIVE RECORDING MATERIAL AND NOVEL CHROMANO COMPOUNDS USED THEREIN

The present invention relates to pressure- or heat-sensitive recording material which contains as colour former in its colour-forming system at least one chromano compound of the general formula

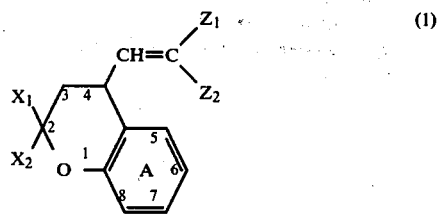

(1)

wherein $X_1$, $X_2$, $Z_1$ and $Z_2$, each independently of the other, represent the group of the formula

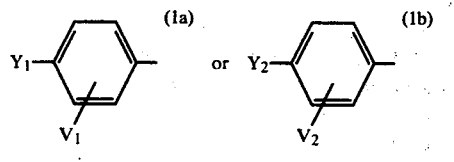

in which $V_1$ and $V_2$, each independently of the other, represent hydrogen, halogen, lower alkyl or lower alkoxy, and $Y_1$ and $Y_2$, each independently of the other, represent hydrogen, $-O-R_1$ or

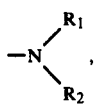

or either $X_1$ and $X_2$ or $Z_1$ and $Z_2$, together with the carbon atom to which each pair of substituents is attached, also represent a divalent radical of the formula

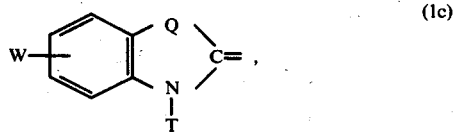

(1c)

in which

Q represents $-O-$, $-S-$ or

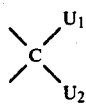

W represents hydrogen, halogen, lower alkyl, lower alkoxy or lower alkoxycarbonyl, T represents alkyl of not more than 12 carbon atoms which is unsubstituted or substituted by halogen, hydroxyl, cyano or lower alkoxy, or represents benzyl which is unsubstituted or substituted by halogen, nitro, lower alkyl or lower alkoxy, and the ring A can be substituted by halogen, nitro, lower alkyl, $-O-R_3$ or

or can contain a fused benzene ring, whilst $R_1$, $R_2$, $R_3$ and $R_4$, each independently of the other, represent hydrogen, alkyl of not more than 12 carbon atoms which is unsubstituted or substituted by halogen, hydroxyl, cyano or lower alkoxy, or represent cycloalkyl, phenyl, benzyl, or phenyl or benzyl which is substituted by halogen, nitro, lower alkyl or lower alkoxy, or each of the pair of substituents $R_1$ and $R_2$ and $R_3$ and $R_4$, together with the nitrogen atom to which said pair is attached, independently represents a 5- or 6-membered, preferably saturated, heterocyclic radical, and $U_1$ and $U_2$, each independently of the other, represent lower alkyl, cycloalkyl, benzyl, or together represent alkylene.

Preferably at least one of the radicals $Y_1$ and $Y_2$ or of the substituents of the ring A is a group of the formula

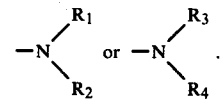

In the definition of the radicals of the chromano compounds, lower alkyl and lower alkoxy usually denote those groups or group components which contain 1 to 5, especially 1 to 3, carbon atoms, for example methyl, ethyl, n-propyl, isopropyl, n-butyl, sec-butyl or amyl, and methoxy, ethoxy or isopropoxy. Halogen in connection with all substituents throughout this specification is for example fluorine, bromine or preferably chlorine.

The radicals $Y_1$ and $Y_2$ can be different or are preferably identical. $V_1$ and $V_2$ are also preferably identical.

Alkyl radicals represented by T and $R_1$ to $R_4$ can be straight-chain or branched. Examples of such alkyl radicals are: methyl, ethyl, n-propyl, isopropyl, n-butyl, sec-butyl, n-hexyl, n-octyl or n-dodecyl.

Substituted alkyl radicals T and $R_1$ to $R_4$ are especially halogenalkyl, cyanoalkyl, hydroxyalkyl, alkoxyalkyl, each containing 2 to 4 carbon atoms, for example β-chloromethyl, β-cyanoethyl, β-hydroxyethyl, β-methoxyethyl or β-ethoxyethyl.

Cycloalkyl represented by $R_1$ to $R_4$ and $U_1$ and $U_2$ is for example cyclopentyl or preferably cyclohexyl.

Preferred substituents in the benzyl moiety of the radicals represented by T and $R_1$ to $R_4$ are for example halogen atoms, nitro, methyl or methoxy groups. Examples of such araliphatic and aromatic radicals are: p-methylbenzyl, o- or p-chlorobenzyl, o- or p-nitrobenzyl, o- or p-tolyl, xylyl, o-, m- or p-chlorophenyl or o- or p-methoxyphenyl, o- or p-nitrophenyl.

A heterocyclic radical represented by each of the pair of substituents $R_1$ and $R_2$ and $R_3$ and $R_4$, together with the nitrogen atom to which said pair is attached, is for example pyrrolidino, piperidino, pipecolino, morpholino, thiomorpholino or piperazino.

The substituents $R_1$ to $R_4$ are preferably benzyl or lower alkyl. The N-substituent T is especially benzyl or alkyl of 1 to 8 carbon atoms, for example n-octyl or, in particular, methyl or ethyl. W is preferably hydrogen and Q is preferably —S— or

The substituents $U_1$ and $U_2$ can be different or are preferably identical. Each of $U_1$ and $U_2$ preferably represents lower alkyl and both represent in particular methyl. Where $U_1$ and $U_2$ together represent alkylene, they contain advantageously 4 or 5 carbon atoms and together with the carbon atom to which they are attached form a cyclopentane or cyclohexane ring.

The ring A is not further substituted or can contain as substituents preferably halogen, nitro, lower alkyl, lower alkoxy or a fused benzene ring. Most preferably the ring A contains in the 7-position an amino group which is preferably mono- or disubstituted, especially by methyl or ethyl.

Chromano compounds having an important utility as colour formers have the general formula

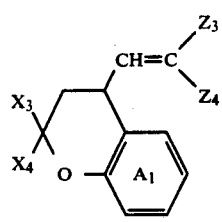

(2)

wherein
  $X_3$, $X_4$, $Z_3$ and $Z_4$, each independently of the other, represent the group of formula

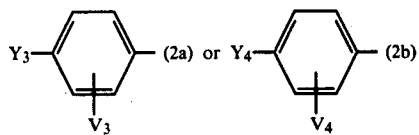

in which
  $V_3$ and $V_4$, each independently of the other, represent hydrogen, halogen, lower alkyl or lower alkoxy,
  $Y_3$ and $Y_4$, each independently of the other, represent hydrogen, —O—$R_5$ or preferably

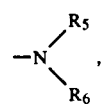

or either $X_3$ and $X_4$ or $Z_3$ and $Z_4$, together with the carbon atom to which each pair of substituents is attached, also represent a divalent radical of the formula

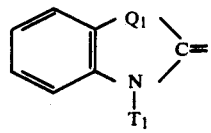

(2c), in which
  $Q_1$ represents —O—, —S— or =C(CH$_3$)$_2$,
  $T_1$ represents alkyl of 1 to 8 carbon atoms or benzyl, and the ring $A_1$ can be substituted by halogen, nitro, lower alkyl, —O—$R_7$ or

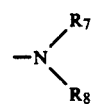

or can contain a fused benzene ring, whilst
  $R_5$, $R_6$, $R_7$ and $R_8$, each independently of the other, represent alkyl of 1 to 12 carbon atoms, cycloalkyl, phenyl, benzyl, or phenyl or benzyl which is substituted by halogen, lower alkyl or lower alkoxy, or
each of the pair of substituents
  $R_5$ and $R_6$ and $R_7$ and $R_8$, together with the nitrogen atom to which said pair is attached, represents a 5- or 6-membered, preferably saturated, heterocyclic radical.

Preferred chromano compounds of the formulae (1) and (2) are those in which each of the X and Z substituents represents respectively a group of the formulae (1a) or (1b) and (2a) or (2b). Those compounds in which all the X and Z substituents are identical are particularly useful colour formers.

Chromano compounds having a particularly interesting utility are those of the general formulae (3), (4) or (5):

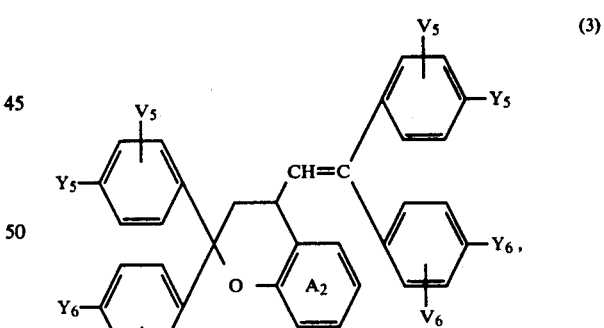

or

-continued

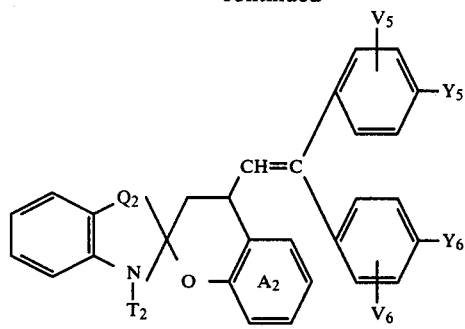

wherein
V$_5$ and V$_6$, each independently of the other, represent hydrogen, chlorine, methyl, methoxy or ethoxy,
Y$_5$ and Y$_6$, each independently of the other, represent lower alkoxy, phenoxy, benzyloxy or

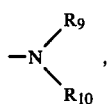

Q$_2$ represents —S— or

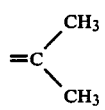

and
T$_2$ represents lower alkyl or benzyl, and the ring A$_2$ can be substituted by halogen, methoxy, nitro or

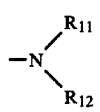

or can contain a fused benzene ring, whilst
R$_9$, R$_{10}$, R$_{11}$ and R$_{12}$, each independently of the other, represent lower alkyl, phenyl or benzyl.

Preferred chromano compounds of the formulae (1), (2), (3), (4) and (5) are those in which the Y substituents represent an amino group

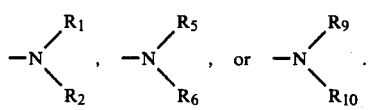

The chromano compounds of the formulae (1) to (5) are partly known compounds, but constitute a novel class of colour formers. They can be obtained by known methods, for example by reacting simultaneously or in succession 1 mole of an aldehyde of the formula

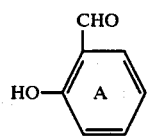

wherein A has the given meaning, with 1 mole of each of the ethylene compounds of the formulae

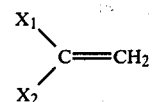

and

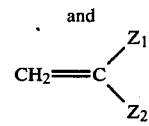

wherein X$_1$, X$_2$, Z$_1$ and Z$_2$ have the given meanings.

The reaction is carried out preferably in a polar solvent, preferably in a lower alcohol, for example methanol or ethanol, and at reflux temperature. Catalytic amounts of a lower aliphatic carboxylic acid, for example acetic acid, can be added to the reaction mixture.

A preferred process for obtaining compounds of the formula (1), wherein the X and Z radicals are identical, consists in reacting 1 mole of an aldehyde of the formula (6) with 2 moles of an ethylene compound of the formula (7) or (8).

One mode of obtaining compounds of the formula (1), wherein either X$_1$ and X$_2$ or Z$_1$ and Z$_2$ represent the radical of the formula (1c), consists in reacting a spiropyrane compound of the formula

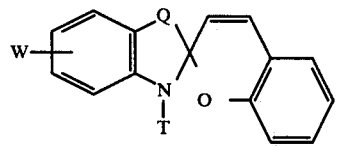

wherein A, W, Q and T have the given meanings, with an ethylene compound of the formula (7) or (8). The reaction is advantageously carried out using catalytic amounts of acetic acid and preferably in a polar solvent, for example ethanol. Depending on the reaction time and the substitution of the spiropyrane compounds, end products of the formula (1) are obtained, in which either each of X$_1$ and X$_2$ represents the radical of the formula (1c) and each of Z$_1$ and Z$_2$ represents the radical of the formula (1a) or (1b) or conversely.

The invention also relates to the novel chromano compounds within the chromano compounds of the formula (1) which have the formula

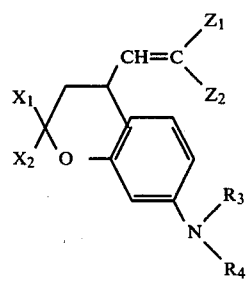

wherein X$_1$, X$_2$, Z$_1$, Z$_2$, R$_3$ and R$_4$ have the given meanings.

Preferred novel chromano compounds have the formula

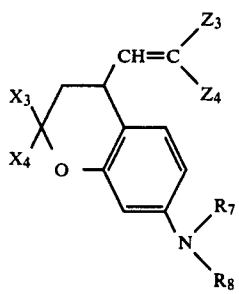 (11)

wherein $X_3$, $X_4$, $Z_3$, $Z_4$, $R_7$ and $R_8$ have the given meanings.

Particularly interesting novel chromano compounds are those of the formula

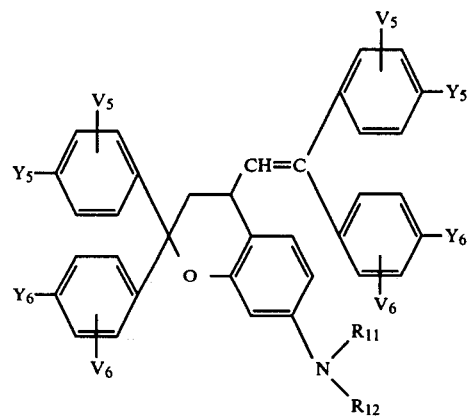 (12)

wherein $Y_5$, $Y_6$, $V_5$, $V_6$, $R_{11}$ and $R_{12}$ have the given meanings.

To be singled out as particularly suitable are the novel chromano compounds of the formula

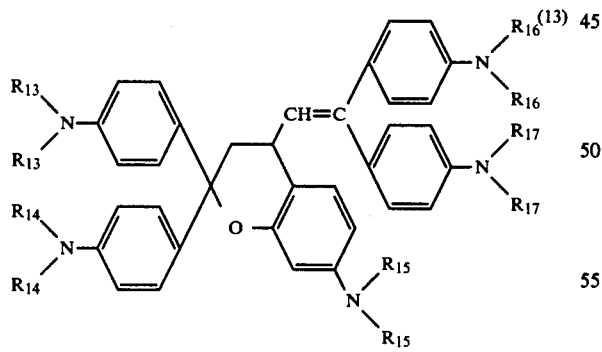 (13)

wherein each of $R_{13}$, $R_{14}$, $R_{15}$, $R_{16}$ and $R_{17}$ represents alkyl of 1 to 4 carbon atoms, in particular methyl or ethyl.

These novel chromano compounds are also particularly useful colour formers.

The process for obtaining the novel chromano compounds of the formula (10) comprises reacting, in any order, 1 mole of an aldehyde of the formula

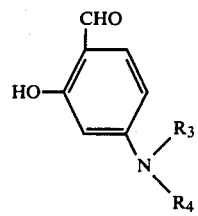 (14)

with 1 mole of each of an ethylene compound of the formulae

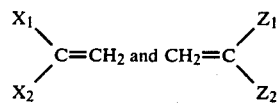

wherein $X_1$, $X_2$, $Z_1$, $Z_2$, $R_3$ and $R_4$ have the given meanings.

The novel compounds of the formulae (11) to (13) are obtained in analogous manner.

The chromano compounds of the formulae (1) to (5) and (10) to (13) are normally colourless or faintly coloured. When these colour formers are brought into contact with a developer, i.e. an electron acceptor, they produce intense yellow to green colours of excellent light fastness. They are therefore also very useful when mixed with other known colour formers, for example 3,3-(bis-amino-phenyl)-phthalides, 3,3-(bis-indolyl)-phthalides, 2,6-di-aminofluoranes or spiropyranes, to produce blue, navy blue, grey or black colourations.

The chromano compounds exhibit an improved colour intensity and lightfastness both on clay and on phenolic substrates. They are chiefly suitable for use in a pressure-sensitive recording material, which can also be a copying material.

A pressure-sensitive material consists for example of at least one pair of sheets, which contain at least one colour former of the formulae (1) to (5) and (10) to (13), dissolved in an organic solvent, and a solid electron acceptor as developer. The colour former effects a coloured marking at those points where it comes into contact with the electron acceptor.

Typical examples of such developers are attapulgite clay, silton clay, silica, bentonite, halloysite, aluminium oxide, aluminium sulphate, aluminium phosphate, zinc chloride, kaolin or any clay or organic compounds with acid reaction, for example unsubstituted or ring-substituted phenols, salicylic acid or esters of salicyclic acid and the metal salts thereof, or an acid polymeric material, for example a phenolic polymer, an alkylphenolacetylene resin, a maleic acid/rosin resin or a partially or completely hydrolysed polymer of maleic acid and styrene, ethylene, vinyl methyl ether or carboxypolymethylene. Preferred developers are attapulgite clay, silton clay or phenolformaldehyde resin. These electron acceptors are preferably applied in the form of a layer to the face of the receiving sheet.

In order to prevent the colour formers contained in the pressure-sensitive recording material from becoming active too soon, they are usually separated from the electron acceptor, for example by incorporating the colour formers in foam-like, sponge-like or honeycomb-like structures. Preferably the colour formers are enclosed in microcapsules.

When the capsules are ruptured by pressure, for example with a pencil, and the colour former solution is thereby transferred to an adjacent sheet which is coated with an electron acceptor, a coloured area is produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example polyhalogenated diphenyl, such as trichlorodiphenyl or a mixture thereof with liquid paraffin; tricresyl phosphate, di-n-butyl phthalate, dioctyl phthalate, trichlorobenzene, nitrobenzene, trichloroethyl phosphate, petroleum ether, hydrocarbon oils, such as paraffin, alkylated derivatives of diphenyl, naphthalene or triphenyl, terphenyls, partially hydrogenated terphenyl, or other chlorinated or hydrogenated condensed aromatic hydrocarbons.

The capsule walls can be formed evenly around the droplets of the colour former solution by coacervation, and the encapsulating material can consist of gelatin and gum arabic, as described e.g. in U.S. Pat. No. 2,800,457.

The capsules can be formed preferably also from an aminoplast or from modified aminoplasts by polycondensation, as described in the British Pat. Nos. 989,264, 1,156,725, 1,301,052 and 1,355,124.

The microcapsules containing the colour formers of formula (1) can be used for the production of a wide variety of known kinds of pressure-sensitive copying material. The various systems differ substantially from one another in the arrangement of the capsules, the colour reactants and the carrier material.

A preferred arrangement is that in which the encapsulated colour former is applied as a layer to the back of a transfer sheet and the electron acceptor substance as a layer to the face of a receiving sheet. However the components can also be used in the paper pulp.

Another arrangement of the constituents consists in the microcapsules which contain the colour former, and the developer, being in or on the same sheet in the form of one or more individual layers or being present in the paper pulp.

Such pressure-sensitive copying materials are described, for example, in U.S. Pat. Nos. 2,730,457, 2,932,582, 3,418,250, 3,427,180 and 3,516,846. Further systems are described in British Pat. Nos. 1,042,596, 1,042,597, 1,042,598, 1,042,599, 1,053,935. Microcapsules which contain the colour formers of formula (1) are suitable for each of these systems as well as for other pressure-sensitive systems.

The capsules are preferably secured to the carrier by means of a suitable adhesive. Since paper is the preferred carrier material, these adhesives are principally paper coating agents, for example gum arabic, polyvinyl alcohol, hydroxymethylcellulose, casein, methyl cellulose or dextrin.

As paper it is possible to use not only normal papers made from cellulose fibres, but also papers in which the cellulose fibres are replaced (partially or completely) by synthetic polymer fibres.

The chromano compounds of the formulae (1) to (5) and (10) to (13) can also be used as colour formers in a thermoreactive recording material, in which, surprisingly, they are distinguished by a high rate of colour development with acid developers and simultaneously by excellent lightfastness. This thermoreactive recording material contains normally at least one carrier, one colour former, one solid electron acceptor and optionally also a binder. Thermoreactive recording systems comprise for example heat sensitive recording and copying materials and papers. These systems are used, for example, for recording information, e.g. in electronic computers, teleprinters or teletwriters, and in measuring instruments. The image (mark) formation can also be effected manually with a heated pen. Laser beams can also be used to produce heat-induced marks.

The thermoreactive recording material can be so composed that the colour former is dispersed or dissolved in one binder layer and the developer is dissolved or dispersed in the binder in a second layer. A second possibility consists in dispersing both the colour former and the developer in the binder in one layer. By means of heat the binder is softened at specific areas and the colour former comes into contact with the electron acceptor at those points where heat is applied and the desired colour develops at once.

Suitable developers are the same electron acceptors as are used in pressure-sensitive papers. Examples of developers are the clays and phenolic resins already mentioned, or phenolic compounds, for example 4-tert-butylphenol, 4-phenylphenol, 4-hydroxydiphenyl ether, $\alpha$-naphthol, $\beta$-naphthol, 4-hydroxymethyl benzoate, 4-hydroxyacetophenone, 2,2'-dihydroxydiphenyl, 4,4'-isopropylidene-diphenol, 4,4'-isopropylidene-bis-(2-methylenephenol), 4,4'-bis-(hydroxyphenyl)valeric acid, hydroquinone, pyrogallol, phloroglucinol, p-, m- and o-hydroxybenzoic acid, gallic acid, 1-hydroxy-2-naphthoic acid, as well as boric acid and aliphatic dicarboxylic acids, for example tartaric acid, oxalic acid, maleic acid, citric acid, citraconic acid or succinic acid.

Fusible, film-forming binders are preferably used for the production of the thermoreactive recording material. These binders are normally water-soluble, whereas the colour formers and the developer are insoluble in water. The binder should be able to disperse and fix the colour former and the developer at room temperature. By applying heat the binder softens or melts, so that the colour former comes in contact with the developer and a colour is able to form. Examples of binders which are soluble or at least swellable in water are hydrophilic polymers, for example polyvinyl alcohol, polyacrylic acid, hydroxyethyl cellulose, methyl cellulose, carboxymethyl cellulose, polyacrylamide, polyvinyl pyrrolidone, gelatin and starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylmethacrylates, ethyl cellulose, nitrocellulose and polyvinyl carbazole. A preferred arrangement, however, is one in which the colour former and the developer are contained in one layer in a water-soluble binder.

The thermoreactive coatings can contain further ingredients. To improve the degree of whiteness, to facilitate the printing of papers, and to prevent the heated pen from sticking, the coatings can contain, for example, talc, $TiO_2$, ZnO or $CaCO_3$ or also organic pigments, for example urea/formaldehyde polymers. In order to effect the colour formation only within a limited temperature range, it is possible to add substances such as urea, thiourea, acetanilide, phthalic anhydride or other appropriate fusible products which induce the simultaneous melting of the colour former and developer.

In the following Manufacturing Directions and Examples, the percentages are by weight unless otherwise indicated.

MANUFACTURING DIRECTIONS

Direction 1

2.7 g of 1,1-bis-(4'-dimethylaminophenyl)-ethylene and 1.9 g of 4-diethylaminosalicylaldehyde are refluxed for 18 hours in 80 ml of ethanol while 4 drops of glacial acetic acid are added. After cooling with ice, the resulting precipitate is collected by filtration, washed with ethanol and dried, affording 2.9 g of a compound of the formula

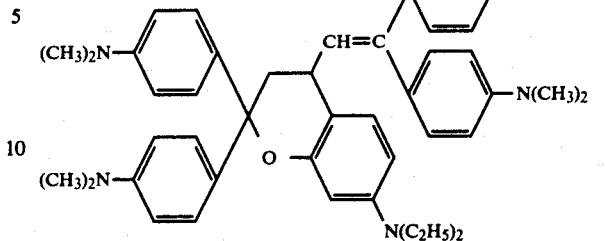
(11)

which melts at 217° to 219° C.

Directions 2 to 7

The colour formers of the formulae (12) to (17) listed in Table 1 are obtained by carrying out the procedure of Direction 1 and replacing the 3-diethylaminosalicylaldehyde by equimolar amounts of each of the following aldehydes:
5-nitro-salicylaldehyde
5-methoxysalicylaldehyde
salicylaldehyde
2-hydroxynaphthaldehyde
3-bromo-5-nitrosalicylaldehyde or
3-nitrosalicylaldehyde.

Table 1

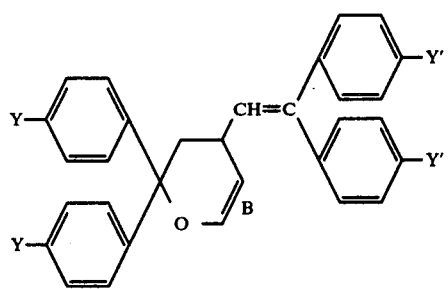

| Formula | Y | Y' | B | Melting Point in °C. |
|---|---|---|---|---|
| (11) | —N(CH₃)₂ | —N(CH₃)₂ | ![benzene with N(C₂H₅)₂] | 217–219 |
| (12) | —N(CH₃)₂ | —N(CH₃)₂ | ![benzene with NO₂] | 225–227 |
| (13) | —N(CH₃)₂ | —N(CH₃)₂ | ![benzene with OCH₃] | 238–239 |
| (14) | —N(CH₃)₂ | —N(CH₃)₂ | ![benzene] | 251–253 |

Table 1-continued

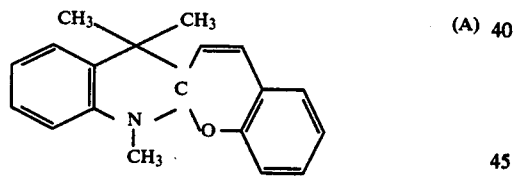

| Formula | Y | Y' | B | Melting Point in °C. |
|---|---|---|---|---|
| (15) | —N(CH₃)₂ | —N(CH₃)₂ | | 269–270 |
| (16) | —N(CH₃)₂ | —N(CH₃)₂ | (methylnaphthyl) | 206–207 |
| (17) | —N(CH₃)₂ | —N(CH₃)₂ | (methyl-bromo-nitrophenyl) | 204–205 |

Direction 8

11.1 g of an indolinospiropyrane compound of the formula (A)

10.7 g of 1,1-bis-(4'-dimethylaminophenyl)-ethylene are refluxed for 2 hours in 300 ml of ethanol with the addition of 1 ml of glacial acetic acid. After cooling with ice, 15.7 g of a compound of the formula

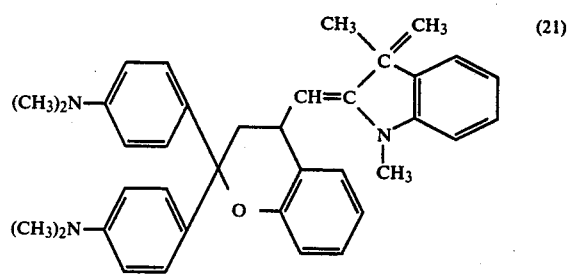

(21)

are isolated by filtration. A sample recrystallised from chloroform/petroleum ether has a melting point of 175°–176° C.

The indolinospiropyrane of the formula (A) can be prepared as follows: 5.2 g of 2-methylene-1,3,3-trimethyl-yl-indoline and 3.7 g of salicylaldehyde are stirred in 25 ml of ethanol for 5 hours at reflux temperature. After cooling, the precipitate is collected by filtration, affording 4.9 g of a compound of the formula (A) which melts at 95°–97° C.

Directions 9 to 12

The colour formers of the formulae (22) to (25) listed in Table 2 are obtained by repeating the procedure of Direction 8 and replacing the indolinospiropyrane compound of the formula (A) by equimolar amounts of compounds of the formulae

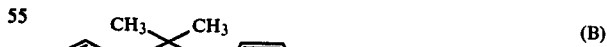

(B)

(C)

-continued

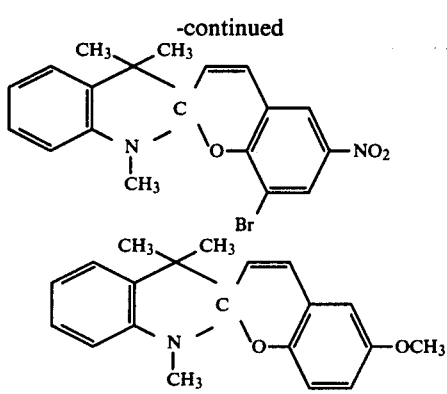

Instead of heating the reaction mixture for 2 hours as in Direction 8, the respective heating times are: 10 minutes for (D), 20 minutes for (B) and (C), and 6 hours for (F).

hours, affording 14.3 g of the compound of the formula (31)

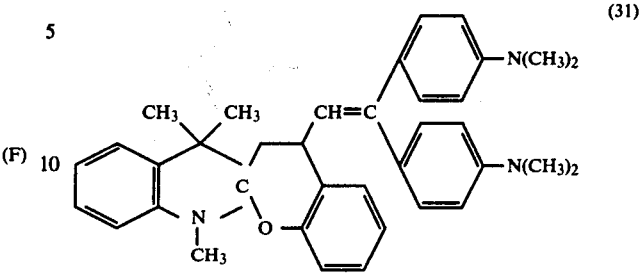

A sample recrystallised from chloroform/petroleum ether melts at 186°–188° C.

Directions 14 to 16

The colour formers of the formulae (32) to (34) listed in Table 3 are obtained by repeating the procedure of Direction 13, but replacing the indolinospiropyrane compound of the formula (A) by respective equimolar amounts of compounds of the formula (B) to (D) and heating the reaction mixture in each case for only 1 to 2 hours.

Table 2

| Formula | Y | B | Melting point in °C. |
|---|---|---|---|
| (21) | —N(CH$_3$)$_2$ | (o-tolyl) | 175–176 |
| (22) | —N(CH$_3$)$_2$ | (2-NO$_2$-phenyl) | 200 (decomp.) |
| (23) | —N(CH$_3$)$_2$ | (4-NO$_2$-phenyl) | 207 (decomp.) |
| (24) | —N(CH$_3$)$_2$ | (4-NO$_2$-3-Br-phenyl) | 110 (decomp.) |
| (25) | —N(CH$_3$)$_2$ | (4-OCH$_3$-phenyl) | 200–201 |

Direction 13

The procedure of Direction 8 is repeated, except that the reaction mixture is heated for 10 hours instead of 2

Table 3

| Formula | Y | B | Melting point in °C. |
|---|---|---|---|
| (31) | —N(CH₃)₂ | (o-methylphenyl) | 186–188 |
| (32) | —N(CH₃)₂ | (methyl-nitrophenyl) | 206–207 |
| (33) | —N(CH₃)₂ | (methyl-nitrophenyl) | 190–192 |
| (34) | —N(CH₃)₂ | (methyl-bromo-nitrophenyl) | 189–190 |

EXAMPLE 1

Production of a thermoreactive paper chromano 6 g of an aqueous dispersion which contains 1.57% of the chromeno compound of formula (11) and 6.7% of polyvinyl alcohol are mixed with 134 g of an aqueous dispersion which contains 14% of 4,4-isopropylidene-diphenol, 8% of attapulgite clay and 6% of polyvinyl alcohol. This mixture is applied to a paper and dried. Contacting the paper with a heated ball-point pen produces a vivid bluish-green colour of excellent lightfastness.

Instead of the above colour former, the colour formers of the formulae (12) to (34) of Tables 1, 2 and 3 can also be used with success.

EXAMPLE 2

Production of a pressure-sensitive copying paper

A solution of 3 g of the chromano compound of formula (14) in 97 g of partially hydrogenated terphenyl is emulsified in a solution of 12 g of pigskin gelatin in 88 g of water of 50° C. A solution of 12 g of gum arabic in 88 g of 50° C. is then added, followed by the addition of 200 ml of water of 50° C. The resultant emulsion is poured into 600 g of ice water, whereupon the coacervation is effected. A sheet of paper is coated with the resultant suspension of microcapsules and dried. A second sheet of paper is coated with silton clay. The first sheet and the sheet of paper coated with silton clay are laid on top of each other with the coated sides face to face.

Pressure is exerted by writing by hand or typewriter and a blue copy of excellent lightfastness develops on the sheet which is coated with clay.

What is claimed is:

1. A pressure- or heat-sensitive recording material which contains as color former at least one chromano compound, at least one electron acceptor, and at least one binder, said chromano compound being of the formula

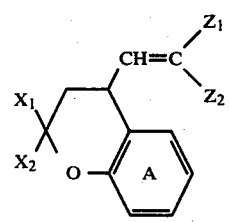

wherein $X_1$, $X_2$, $Z_1$ and $Z_2$, each independently of the other, represent the group of the formula

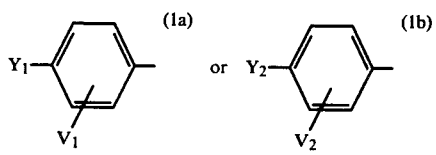

in which
V$_1$ and V$_2$, each independently of the other, represent hydrogen, halogen, lower alkyl or lower alkoxy, and
Y$_1$ and Y$_2$, each independently of the other, represent hydrogen, —O—R$_1$ or

and the ring A is unsubstituted or substituted by halogen, nitro, lower alkyl, —O—R$_3$ or

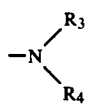

or contains a fused benzene ring, whilst
R$_1$, R$_2$, R$_3$ and R$_4$, each independently of the other, represent hydrogen, alkyl of not more than 12 carbon atoms which is unsubstituted or substituted by halogen, hydroxyl cyano or lower alkoxy, or represent cycloalkyl, phenyl, benzyl, or phenyl or benzyl which is substituted by halogen, nitro, lower alkyl or lower alkoxy, or
each of the pair of substituents
R$_1$ and R$_2$ and R$_3$ and R$_4$, together with the nitrogen atom to which said pair is attached, independently represents a 5- or 6-membered heterocyclic radical.

2. A recording material as claimed in claim 1, wherein X$_1$, X$_2$, Z$_1$ and Z$_2$, each independently of the other, represent the group of the formula

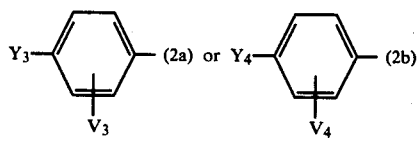

V$_3$ and V$_4$, each independently of the other, represent hydrogen, halogen, lower alkyl or lower alkoxy,
Y$_3$ and Y$_4$, each independently of the other, represent hydrogen, —O—R$_5$ or

the ring A is unsubstituted or substituted by halogen, nitro, lower alkyl, —O—R$_7$ or

or contains a fused benzene ring, whilst
R$_5$, R$_6$, R$_7$ and R$_8$, each independently of the other, represent alkyl of 1 to 12 carbon atoms, cycloalkyl, phenyl, benzyl, or phenyl or benzyl which is substituted by halogen, lower alkyl or lower alkoxy, or
each of the pair of substituents
R$_5$ and R$_6$ and R$_7$ and R$_8$, together with the nitrogen atom to which said pair is attached, represents a 5- or 6-membered heterocyclic radical.

3. A recording material as claimed in claim 1, wherein X$_1$, X$_2$, Z$_1$ and Z$_2$ are identical.

4. A recording material as claimed in claim 1 wherein the colour former has the formula

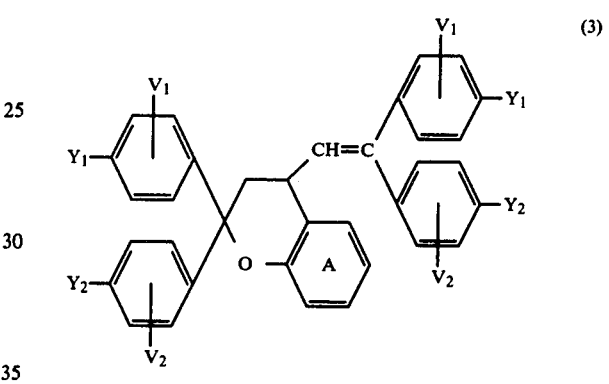

wherein
V$_1$ and V$_2$, each independently of the other, represent hydrogen, chlorine, methyl, methoxy or ethoxy,
Y$_1$ and Y$_2$, each independently of the other, represent lower alkoxy, phenoxy, benzyloxy or

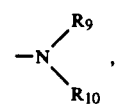

and the ring A is unsubstituted or substituted by halogen, methoxy, nitro or

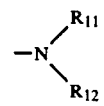

or contains a fused benzene ring, whilst
R$_9$, R$_{10}$, R$_{11}$ and R$_{12}$, each independently of the other, represent lower alkyl, phenyl or benzyl.

5. A recording material as claimed in claim 1 wherein Y$_1$ and Y$_2$ represent an amino group

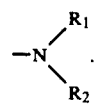

6. A recording material as claimed in claim 2 wherein Y$_3$ and Y$_4$ represent an amino group

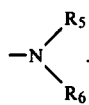

7. A recording material as claimed in claim 4 wherein $Y_1$ and $Y_2$ represent an amino group

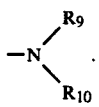

8. A recording material as claimed in claim 1 wherein the ring A carries an amino group in the 7-position which is mono- or disubstituted by lower alkyl.

9. A recording material as claimed in claim 1 wherein the colour former has the formula

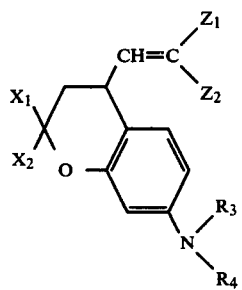

in which $X_1$, $X_2$, $Z_1$, $Z_2$, $R_3$ and $R_4$ are as defined in claim 1.

10. A recording material as claimed in claim 2 wherein the colour former has the formula

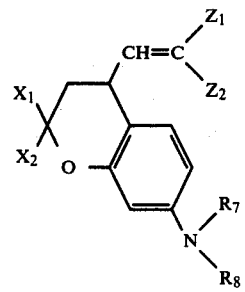

wherein $X_1$, $X_2$, $Z_1$, $Z_2$, $R_7$ and $R_8$ are as defined in claim 2.

11. A recording material as claimed in claim 4 wherein the colour former has the formula

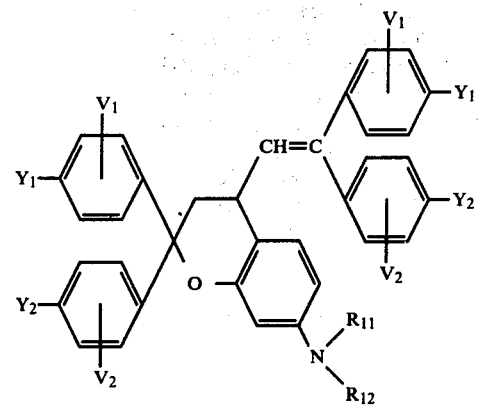

wherein $Y_1$, $Y_2$, $V_1$, $V_2$, $R_{11}$ and $R_{12}$ are as defined in claim 5.

12. A recording material as claimed in claim 11 wherein the colour former has the formula

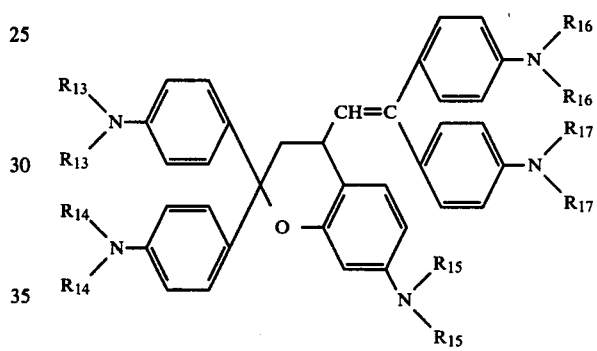

wherein each of $R_{13}$, $R_{14}$, $R_{15}$, $R_{16}$ and $R_{17}$ represents alkyl of 1 to 4 carbon atoms.

13. A recording material as claimed in claim 1 wherein at least one of the substituents $Y_1$ and $Y_2$ or of the substituents in the ring A represents

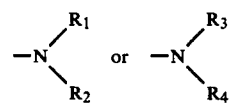

in the chromano compound.

14. A pressure-sensitive recording material as claimed in claim 1, which contains at least one said chromano compound dissolved in an organic solvent.

15. A pressure-sensitive recording material as claimed in claim 14, wherein the solution of the chromano compound in an organic solvent is contained in microcapsules which can be ruptured by pressure.

16. A pressure-sensitive recording material as claimed in claim 14, wherein the electron acceptor is attapulgite clay, silton clay, or a phenolformaldehyde resin.

17. A pressure-sensitive recording material as claimed in claim 15, wherein the encapsulated chromano compound is in the form of a layer on the reverse side of a transfer sheet and the electron acceptor is in the form of a layer on the face of the receiving sheet, the sheets being arranged such that in use the coated sides contact each other.

18. A pressure-sensitive recording material as claimed in claim 1, which contains said chromano compound together with one or more other colour formers.

19. A heat-sensitive recording material as claimed in claim 1, which contains in at least one layer at least one said chromano compound, at least one electron acceptor and at least one binder.

20. A heat-sensitive recording material as claimed in claim 19, wherein the electron acceptor is attapulgite clay, silton clay, a phenolic compound, a phenolic resin or a solid organic acid.

21. A heat-sensitive composition which contains at least one chromano compound as defined in claim 1, at least one electron acceptor and, at least one binder.

22. A chromano compound of the formula

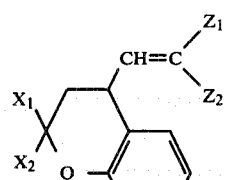

wherein
 $X_1$, $X_2$, $Z_1$ and $Z_2$, each independently of the other, represent the group of the formula

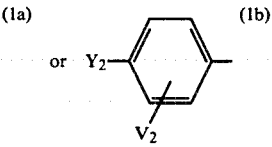

in which
 $V_1$ and $V_2$, each independently of the other, represent hydrogen, halogen, lower alkyl or lower alkoxy, and
 $Y_1$ and $Y_2$, each independently of the other, represent hydrogen, —O—$R_1$ or

$R_1$, $R_2$, $R_3$ and $R_4$, each independently of the other, represent hydrogen, alkyl of not more than 12 carbon atoms which is unsubstituted or substituted by halogen, hydroxyl, cyano or lower alkoxy, or represent cycloalkyl, phenyl, benzyl, or phenyl or benzyl which is substituted by halogen, nitro, lower alkyl or lower alkoxy, or
each of the pair of substituents
 $R_1$ and $R_2$ and $R_3$ and $R_4$, together with the nitrogen atom to which said pair is attached, independently represents a 5- or 6-membered heterocyclic radical.

23. A chromano compound as claimed in claim 22, wherein
 $X_1$, $X_2$, $Z_1$ and $Z_2$, each independently of the other, represent the group of the formula

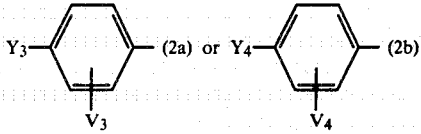

$V_3$ and $V_4$, each independently of the other, represent hydrogen, halogen, lower alkyl or lower alkoxy,
 $Y_3$ and $Y_4$, each independently of the other, represent hydrogen, —O—$R_5$ or

$R_3$, $R_4$, $R_5$ and $R_6$, each independently of the other, represent alkyl of 1 to 12 carbon atoms, cycloalkyl, phenyl, benzyl, or phenyl or benzyl which is substituted by halogen, lower alkyl or lower alkoxy, or
each of the pair of substituents
 $R_3$ and $R_4$ and $R_5$ and $R_6$, together with the nitrogen atom to which said pair is attached, represents a 5- or 6-membered heterocyclic radical.

24. A chromano compound as claimed in claim 23, of the formula

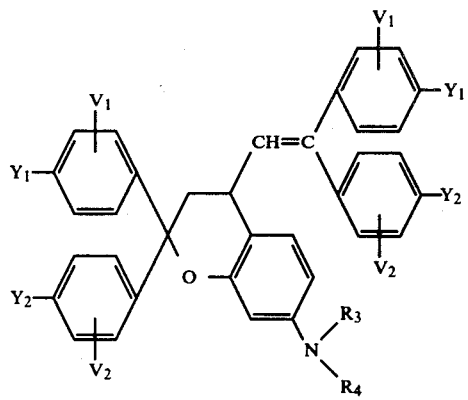

wherein
 $V_1$ and $V_2$, each independently of the other, represent hydrogen, chlorine, methyl, methoxy or ethoxy,
 $Y_1$ and $Y_2$, each independently of the other, represent lower alkoxy, phenoxy, benzyloxy or

and
 $R_3$, $R_4$, $R_9$ and $R_{10}$, each independently of the other, represent lower alkyl, phenyl or benzyl.

25. A chromano compound as claimed in claim 24, of the formula

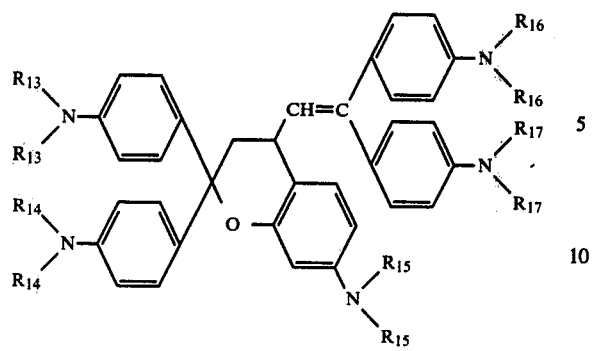
wherein each of $R_{13}$, $R_{14}$, $R_{15}$, $R_{16}$ and $R_{17}$ represents alkyl of 1 to 4 carbon atoms.
* * * * *